United States Patent
Pedroza Rodriguez et al.

(10) Patent No.: US 10,087,094 B2
(45) Date of Patent: Oct. 2, 2018

(54) CONSORTIUM OF FUNGI IMMOBILIZED ON A LAMINAR LIGNOCELLULOSE CARRIER FOR THE TREATMENT OF WASTEWATER AND METHOD FOR PRODUCING SAME

(71) Applicant: PONTIFICIA UNIVERSIDAD JAVERIANA, Bogotá (CO)

(72) Inventors: Aura Marina Pedroza Rodriguez, Bogotá (CO); Ingrid Johana Puentes Cardenas, Bogotá (CO)

(73) Assignee: PONTIFICIA UNIVERSIDAD JAVERIANA, Bogotá (CO)

( * ) Notice: Subject to any disclaimer, the term of this patent is extended or adjusted under 35 U.S.C. 154(b) by 0 days.

(21) Appl. No.: 15/103,712

(22) PCT Filed: Dec. 9, 2014

(86) PCT No.: PCT/IB2014/002720
§ 371 (c)(1),
(2) Date: Jun. 10, 2016

(87) PCT Pub. No.: WO2015/087143
PCT Pub. Date: Jun. 18, 2015

(65) Prior Publication Data
US 2016/0280574 A1    Sep. 29, 2016

(30) Foreign Application Priority Data
Dec. 11, 2013  (CO) .................... 13290121

(51) Int. Cl.
*C02F 3/34* (2006.01)
*C12N 1/14* (2006.01)
(Continued)

(52) U.S. Cl.
CPC ............... *C02F 3/347* (2013.01); *C02F 3/04* (2013.01); *C02F 3/103* (2013.01); *C02F 3/34* (2013.01);
(Continued)

(58) Field of Classification Search
CPC .. C02F 3/347; C02F 3/34; C02F 3/103; C02F 2103/30; C02F 3/04; C02F 2101/20; C02F 2101/308; C02F 2203/006
(Continued)

(56) References Cited

U.S. PATENT DOCUMENTS

2005/0067347 A1 *  3/2005  Vanhulle ................ C02F 1/78
                                                                    210/606

FOREIGN PATENT DOCUMENTS

EP    1679287 A1 *  7/2006
FR    2772623 A1 *  6/1999

OTHER PUBLICATIONS

Iqbal, M et al., Entrapment of fungal hyphae in structural fibrous network of papaya wood to produce a unique biosorbent for the removal of heavy metals. (Sep. 2006) Enzyme and Microbial Technology, Sep. 4, 2006 Stoneham, MA, US, vol. 39 No. 5, pp. 996-1001 ISSN 0141-0229.*
(Continued)

*Primary Examiner* — Fred Prince
(74) *Attorney, Agent, or Firm* — Birch, Stewart, Kolasch & Birch, LLP

(57) ABSTRACT

The invention relates to a laminar biocarrier made by weaving or interlacing yarns of lignocellulosic material, which supports and immobilizes a consortium of wood-decay fungi, in particular strains of *Pleurotusostreatus* and *Phanerochaetechrysosporium*, for the treatment of wastewater contaminated by colorants, heavy metals, chemical oxygen demand and biological oxygen demand. The invention also relates to a method for producing the inoculated laminar biocarrier and to the use thereof as a filter for reactors of different configurations for the treatment of waste effluents.

19 Claims, 1 Drawing Sheet

(51) Int. Cl.
*C12N 11/12* (2006.01)
*C02F 3/10* (2006.01)
*C02F 3/04* (2006.01)
*C02F 103/30* (2006.01)
*C02F 101/20* (2006.01)
*C02F 101/30* (2006.01)

(52) U.S. Cl.
CPC ............... *C12N 1/14* (2013.01); *C12N 11/12* (2013.01); *C02F 2101/20* (2013.01); *C02F 2101/308* (2013.01); *C02F 2103/30* (2013.01); *C02F 2203/006* (2013.01); *Y02W 10/15* (2015.05)

(58) Field of Classification Search
USPC ........ 210/602, 615, 150, 151; 435/177, 178, 435/179
See application file for complete search history.

(56) References Cited

OTHER PUBLICATIONS

Lu, Y et al., Biodegradation of phenolic compounds from coking wastewater by immobilized white rot fungus *Phanerochaete chrysosporium*, Journal of Hazardous Materials. (Jun. 2009), Elsevier, Amsterdam, NL vol. 165 No. 1-3, pp. 1091-1097 ISSN 0304-3894 Doi: doi:10.1016/j.jhazmat.2008.10.091 Yang Gordon C C.*

Nigam, P. et al., Physical removal of textile dyes from effluents and solid-state fermentation of dye-absorbed agricultural residues. (Apr. 2000) Bioresource Technology May 2000 Elsevier Sci Ltd May 2000 vol. 72 No. 3, pp. 219-226 ISSN 09608524 (print) Doi:doi:10.1016/S0960-8524(99)00123-6.*

Eduard Borras et al., Soil colonization by Trametes versicolor grown on lignocellulosic materials: Substrate selection and naproxen degradation. (Jun. 2011) International Biodeterioration and Biodegradation, Jun. 17, 2011 Esevier Ltd, GB Jun. 17, 2011 vol. 65 No. 6 pp. 846-852 ISSN 0964-8305 Doi; doi: 10.1016/j.ibiod.2011.06.005.*

* cited by examiner

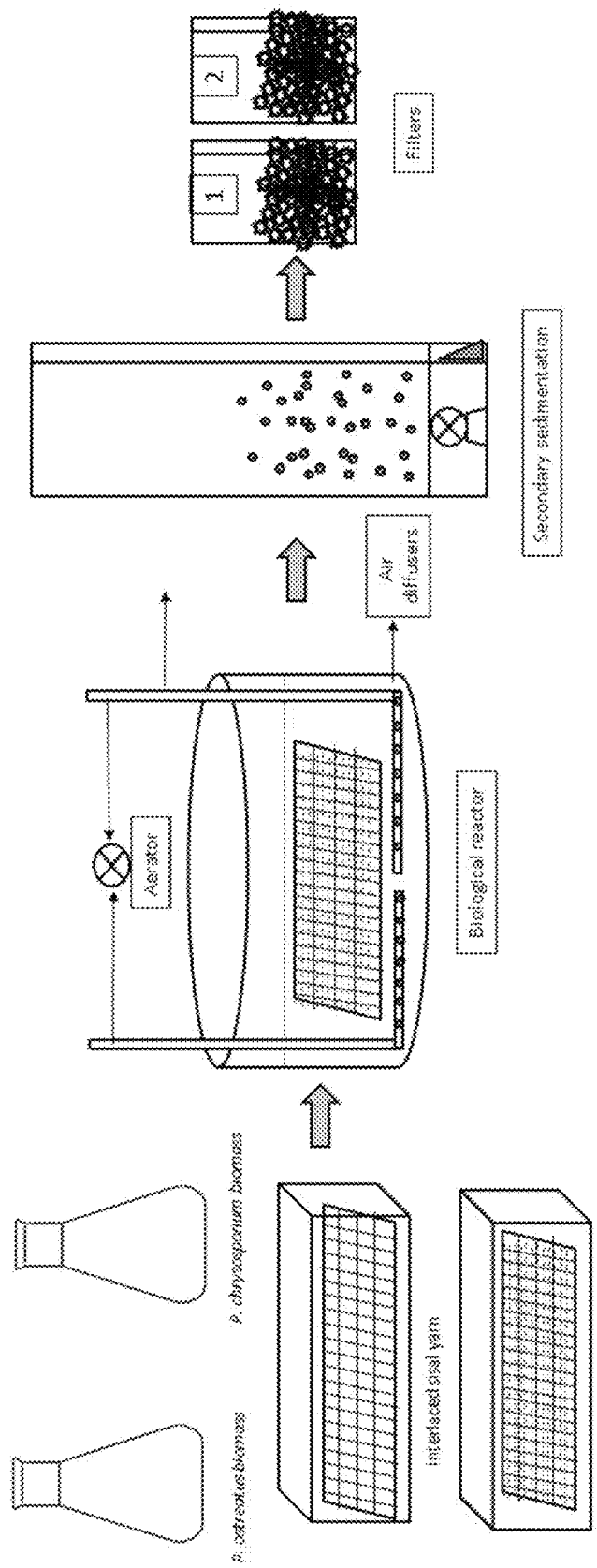

CONSORTIUM OF FUNGI IMMOBILIZED ON A LAMINAR LIGNOCELLULOSE CARRIER FOR THE TREATMENT OF WASTEWATER AND METHOD FOR PRODUCING SAME

FIELD OF THE INVENTION

The present invention relates to a consortium of wood-decay fungi immobilized on a laminar lignocellulose carrier for the treatment of wastewaters contaminated by colorants, heavy metals, chemical oxygen demand (COD) and biological oxygen demand (BOD).

BACKGROUND OF THE INVENTION

The textile industry is one of the oldest in the world. The oldest known textiles, which date back to about 5,000 B.C., are scraps of linen cloth found in Egyptian caves. The industry was primarily a family and domestic one until the early part of the 1500s when the first factory system was established. However, it was not until the XVIII century that power machines for weaving or spinning were invented, machines that replaced manual power (Neefus, J. D. "Textile Industrial Processes," in Aspects of Industrial Hygiene Plant Operations, Volume 1, 1982).

The method for manufacturing textile products comprises a large number of unit operations using several raw materials, such as cotton, wool, synthetic fibers, or mixtures thereof. The environmental impact of their liquid effluents varies by the wide variety of raw materials, reagents and methods of production. In the effluents, there can be found salts, starch, peroxides, EDTA, surfactants, enzymes, dyes, metals and other organic compounds of different structures that come from several steps of the overall process (Mansilla, H D, et al., "Tratamiento de residuos líquidos de la industria de celulosa y textil" en Eliminación de Contaminación por Fotocatálisis Heterogena, CYTED, 2001)

In general, discharge watercourses come mainly from degumming (15%), scouring and mercerizating (20%), and from bleaching, dyeing and washing (65%). The greatest contribution of the organic load comes from the degumming step, which provides about 50% of the BOD (O'Neill C., et al., J. Chem. Technol. Biotechnol., 1999).

The amount of water used in textile processes considerably changes depending on the specific process and equipment used by the plant. For example, around 100 and 150 liters of water per kilogram of product is used when dyeing with disperse dyes. When dyeing with reactive dyes, the range varies from 125 to 170 liters per kilogram of product (EPA Profile of the Textile Industry, 1997).

The textile industry does not release large quantities of metals; however, even small involved concentrations may produce accumulations in the tissues of aquatic animals. The high content of nitrogen in the discharge can increase the population of fish and seaweed, and deplete the oxygen dissolved in the water at a long-term period. Textile dyes last long in the environment, and classic elimination methods are not useful due to the fact that partial oxidations or reductions may generate highly toxic products (O'Neill C., et al., J. Chem. Technol. Biotechnol., 1999).

Most of colorants currently used in the textile industry are synthetic, water-soluble, highly resistant to chemical agents and poorly biodegradable. About 60% of colorants that are being used comprise in their structure highly reactive azo, anthraquinone or phthalocyanine groups that form an ether type union with the fiber (Mansilla, H D, et al., "Tratamiento de residuos líquidos de la industria de celulosa y textil" en Eliminación de Contaminación por Fotocatálisis Heterogena, CYTED, 2001).

Several physicochemical techniques are used for removal of synthetic dyes, such as coagulation and flocculation combined with filtration and flotation, precipitation-flocculation with $Fe(II)/Ca(OH)_2$, ozone oxidation, membrane filtration and reverse osmosis, among others, all of which produce effluents with good quality (Fernandez, J. A., et al., Rev. Colomb. Biotechnol. 2009).

However, most of these techniques are highly expensive, reason why some other alternative treatments are sought, such as the use of biological treatments, which are usually cheaper due to their inexpensive raw materials, and can be worked with resources that in many cases turn out to be wastes from other activities (Moeller, G., Garzón, M. Anuario Lmta, 2003).

Most of the microorganisms (m.o) used in the bioremediation of contaminated effluents are wood-decay fungi, a group of heterogeneous m.o having in common the ability to degrade lignin and other components from the trees, such as cellulose. They produce extracellular enzymes that oxidize phenolic compounds. Among the characterized enzymes are laccases, manganese peroxidases, lignin peroxidases and peroxide-generating enzymes. The activity of these m.o on colorants is based on the non-specificity of the enzyme system for depolymerizing and mineralizing lignin (Moeller, G., Garzon, M. Anuario Lmta, 2003). It has been seen that in most fungi the ligninolysis occurs during the second metabolism, i.e., during nutrient limitation, allowing the fungi to only synthesize and secrete ligninolytic agents starting polymer degradation (Sathiya, P., et al., Rev. Iberoamericana, 2006).

Immobilization of m.o on organic or inorganic supports for the treatment of urban and industrial wastewater has shown good results in terms of color removal, phenols and chlorinated compounds, showing advantages such as increased metabolic activity of the immobilized m.o, easy recovery of m.o and biocarriers, contact surface, persistence within the system, increased resistance to toxicity, and environmental changes.

In the case of filamentous microorganisms, immobilization can be taken for the production of polysaccharides that act as glue within the attachment with the support or by adsorption to supports with high porosity that allow the filaments to enter into the support and to keep retained by physical, hydrophobic, Van der Waals, hydrogen bonding, ligand exchange, ion exchange or chemisorption interactions (Herrera, A., Rosas, J. Pontificia Universidad Javeriana, 2003).

The availability, cost and efficiency in mass retention should be taken into account among the criteria for choosing the immobilization support. Pita from sisal leaves (*Furcraea* spp.) is the Colombian natural fiber par excellence, which originates in the tropical America, the Andean region of Colombia and Venezuela. Sisal is cultivated in Colombia, and has been extracted since time immemorial for the manufacture of hammocks, nets, ropes, sandals, jiqueras (bags), sacks and packsaddles (MAVT, MINAGRICULTURA, DEPTO PLANEACIÓN, Republic of Colombia, 2006).

The sisal is a perennial plant that reaches up to 5 meters high, and its stalk, which is succulent, fibrous and with several floral scars, reaches up to 40 cm in diameter. Its leaves or succulent green fleshy leaves and with parallel nervations reach up to 2.5 meters long; they look like rigid lances (lanceolate), and also have many hooked thorns in their margins, which become red when water is scarce. Its succulent flowers have about 3 cm in diameter, are fragrant, have 3 petals and 3 greenish white sepals, and its stamens are yellow. They are arranged in straight and branched inflorescences (scape or century plant) that can reach up to 15 meters high. Its fruits are about 2 cm in diameter and its seeds germinate in the same plant, propagules fall to the ground already formed, reason why it is considered as a viviparous plant (Mahecha et al., 2004. Available at Red Nacional de Jardines Botánicos).

The sisal leaf is composed by water (85%), cellulose (6%), protein, saponins and sapogenins (8%), and minerals (1%). The extracted sisal fiber represents a maximum of 4% of the total weight of the leaf, and its main structure corresponds to cellulose, lignin and pentosans. Each filament consists of elementary fibrils bonded together by lignin, and the ends of the fibrils are superposed to form multicellular filaments along the leaf, which form the sisal fiber (MAVT, MINAGRICULTURA, DEPTO PLANEACIÓN, Republic of Colombia, 2006).

In the field of biological treatment of industrial waste with immobilized m.o on cellulose supports, Patent WO03/035561 teaches a method for treatment of dyes and colorants of the textile industry with different physicochemical characteristics. The first step of the process involves pretreating the residues with ozone or adsorption of the waste on biodegradable supports, membrane filtration (micro or nanofiltration), osmose, electrolytic processes, sodium borohydride process, electrolysis, electrochemical oxidation and electrodialysis, among others. Pretreatment is performed for 10 minutes to 72 hours, and when performed with ozone it may last 1 to 3 hours, in the case of a discoloration effect.

The second step of the treatment involves contacting the wastewater with wood-decay fungi, specifically with *Clitocybuladusenii, Trichodermaharanium* and *Trichodermalongibrachiatum* species. Fungi is cultivated at about 20 and 45° C. and at a pH 4 to 9, nitrogen, carbon and mineral salts sources are used for their growth. During treatment, wood-decay fungi can be added to the pretreated waters in polymer matrices and encapsulated form.

The polymers comprising such matrices are made from biodegradable, natural and non-toxic materials and are selected from the group consisting of alginates, maltodextrins, corn starch, kappa carrageenan and iota carrageenan salts. Other polymers that may be useful are cellulose or polypropylene derivatives on which the culture is inoculated in order to continue treatment. These biological substrates of cellulosic materials such as polypropylene achieve immobilizing the culture because they form a mesh or woven web that facilitates the growth of the fungi.

The WO03/035561 patent also teaches that it can be possible to use hydrolytic enzymes, cellulolytic enzymes and ligninolytic enzymes activity for the removal of pollutants. The organisms used for the treatment corresponds to lignicolous wood-decay fungi chosen from the group consisting of: fungi of the genus *PleurotusyPhanerochaete.*

The WO94/25190 teaches a method treating solid materials with organic contaminants comprising intimately mixing the contaminated material with an actively-growing fungal biomass in a ratio of 1:1 to 10:1 under aerobic conditions, wherein the biomass comprises a lignocellulosic substrate throughout which are distributed spores or propagules of a lignolytic fungus of the genus *Phanerochaete*. Additionally, biomass includes a mixture of bacteria which act to maintain the temperature of the mixture at 5 to 40° C., and bacteria or enzymes which utilize as a substrate the degradation products of the contaminants. Aeration and moisture of the mix are controlled resulting in the production of free radicals and cleaving of complex contaminant structures such as chlorophenols and polyaromatic hydrocarbons. At the end of the process, the support material is degraded and fungi introduced decline in numbers due to competition from the natural population.

The US2008264858 patent discloses a burlap bags or sacks for the treatment of agricultural and urban wastewater, comprising: (i) a filling with biodegradable material selected from woodchips, sawdust, straw, paper, cardboard, agricultural waste products, wood wastes, composts and combinations thereof, inoculated with a saprophytic fungus selected from the group consisting of *Pleurotus ostreatus, Pleurotus pulmonarius, Pleurotus dryinus, Pleurotus tuberregium, Piptoporus betulinus, Fomitopsis pinicola, Fomitopsis officinalis, Trametes versicolor, Hypsizygus ulmarius, Ganoderma lucidum, Ganoderma applanatum, Ganoderma curtisii, Ganoderma oregonense* and *Ganoderma tsugae*; (ii) seeds of grasses, bushes, trees, or hyperaccumulator plants and combinations thereof.

The CN101549936 patent discloses a method for wastewater treatment in which the effluent pH is initially adjust between 4 and 5.5, and inoculated supports are added with a white-rot fungi (*Phanerochaetechrysosporium*), and the temperature is adjusted between 35 and 60° C. with constant shaking speed of 170 rpm. The m.o growth is performed in a potato flour leaching culture medium (potato 4 g/100 ml, glucose 2 g/100 ml, $KH_2PO_4$: 0.3 g/100 ml, $MgSO_4$: 0.15 g/100 ml; and yeast medium components (glucose 0.5 g/100 ml, $KH_2PO_4$: 0.1 g/100 ml, $(NH_4)_2SO_4$: 0.1 g/100 ml, $MgSO_4*7H_2O$ 0.05 g/100 ml, yeast extract 0.02 g/100 ml), pH 5.0-6.0, previously sterilized at 121° C. for 20 min and cooled to a temperature between 28 and 34° C. (0.05 g ratio of fungus per 250 mL of culture medium, constant shaking for 3 days).

The inoculated m.o is a support comprising: (i) a corn core pre-treated with NaOH 3%, $H_2SO_4$ 3% and industrial alcohol 75%, oven dried at 50° C. and sterilized at 121° C. for 15 min, and (ii) a coating around the core consisting of copper mesh and nylon thread, where the support comprises 0.3 g of core and a coating of about 0.2 and 1.8 g of copper mesh and 0.2 to 1.1 of nylon thread.

The FR2772623 patent discloses a method for treating recalcitrant contaminants such as soil aromatic polycyclic hydrocarbons, comprising the steps of: (i) pasteurizing a lignified organic support (16 h cycles at about 65 and 85° C.) selected from wood chips, bark or corn cobs; (ii) inoculating the organic support with a fungus of the Polypore family, preferably Coriolusversicolor, which is in the form of: (a) a solution of spores and/or mycelial fragments suspended in a liquid medium, (b) mycelium previously developed in a liquid medium, (c) mycelium previously set on a solid support (gelled solid medium or sterilized cereal grains); (Iii) incubating the inoculated support in suitable conditions for fungal growth; and (iv) introducing the inoculated support in contaminated soils to be treated in a ratio between 1 and 50%, preferably between 5 and 20% (wt %).

The CN1544610 patent teaches a method for degradating stalks comprising mixing the waste material with a liquid culture containing *lactobacillus, Streptococcusfaecali* and *Candidautilis* in 1 to 20000 proportions (inoculum: substrate) with addition of 0.9% NaCl at 25-30° C. for 7 to 10 days. Subsequently, it is mixed with wood-decay fungi (*PhanerochaeteyloPleurotus*) and fermented at 25-30° C. until degradation of the plant material.

Moreover, the DE10125365 patent teaches the combination of fungi with monooxygenase/dioxygenase activity (*Trametesversicolor; Pleurotusostreatus* or *Phanerochaetechrysosporium*) and Zygomycotina fungi with glutathione-S-transferase activity (*Cephalosporium, Penicillium, TrichodermayMucor*) for the degradation of xenobiotics, wherein the most efficient bioremediation of contaminated soils and water was the combination of *Phanerochaetechrysosporiumy Mucorhiemalis* f.

Notwithstanding the foregoing, there is still the need to develop specific combinations of microorganisms like wood-decay fungi for treating water with high COD and BOD values, contaminated with azo, triphenylmethane, aniline or anthraquinone colorants in mixes that comprise additives and heavy metals—for example wastewater from the textile industry, plastic arts industries and industries that generate contaminated water with heavy metals, among others—, conditions under which individual treatments with fungal strains do not generate efficient results.

BRIEF DESCRIPTION OF THE INVENTION

The present invention discloses a laminar biocarrier holding and immobilizing a consortium of wood-decay fungi. The laminar biocarrier is made by interlacing sisal yarns forming an elastic, flexible, resistant mesh having high porosity and malleability. These meshes are coated with a biomass layer of wood-decay fungi such as *P. ostreatus, P. chrysosporium, Trametesversicolor, Ganodermalucidum, Lentulaedodes, Phlebia radiata* and *Irpexlacteus*, preferably *P. ostreatus* and *P. chrysosporium*, which are hypertolerant to heavy metals, laccase producers, lignin peroxidase, and manganese peroxidase with bleaching and adsorption capacity. The laminar biocarrier can be used in reactors with different configuration such as cylindrical and square for the removal of the color generated by azo, triphenylmethane, and anthraquinone colorants, among others.

Additionally, the biocarrier of the invention has important adsorption properties by the joint action of the lignocellulosic material, the viable and hypertolerant biomass of both fungi; thus, the laminar biocarrier efficiently removes heavy metals such as cadmium, nickel, lead, copper and chromium in industrial wastewater in the presence of colorants and additives.

BRIEF DESCRIPTION OF THE DRAWINGS

FIG. 1 shows the laminar biocarrier of the invention.

SUBJECT MATTERS OF THE INVENTION

In a first aspect, the invention relates to a consortium of wood-decay fungi, namely, *P. ostreatus, P. chrysosporium, Trametesversicolor, Ganodermalucidum, Lentulaedodes, Phlebia radiata* and *Irpexlacteus* strains, preferably *P. ostreatus* and *P. chrysosporium*, for treating wastewater.

In a second aspect, the invention provides a laminar biocarrier made by weaving or interlacing sisal yarns holding and immobilizing fungal strains such as *P. ostreatus, P. chrysosporium, Trametesversicolor, Ganodermalucidum, Lentulaedodes, Phlebia radiata* and *Irpexlacteus*, preferably *P. ostreatus* and *P. chrysosporium*, for treating wastewater.

In a third aspect, the invention provides a filter made from the sisal laminar biocarrier inoculated with fungal strains for treating wastewater.

In a fourth aspect, the invention discloses a method for preparing a laminar biocarrier inoculated with *P. ostreatus, P. chrysosporium, Trametesversicolor, Ganodermalucidum,* *Lentulaedodes, Phlebia radiata* and *Irpexlacteus* strains, preferably *P. ostreatus* and *P. chrysosporium*, for treating wastewater.

It is also part of the invention the use of the combination of *P. ostreatus, P. chrysosporium, Trametesversicolor, Ganodermalucidum, Lentulaedodes, Phlebia radiata* and *Irpexlacteus* strains, preferably *P. ostreatus* and *P. chrysosporium*, in a laminar biocarrier prepared by weaving or interlacing sisal yarns for treating wastewater.

DETAILED DESCRIPTION OF THE INVENTION

In a first aspect, the invention teaches a consortium of wood-decay fungi: *P. ostreatus, P. chrysosporium, Trametesversicolor, Ganodermalucidum, Lentulaedodes, Phlebia radiata* and *Irpexlacteus*, preferably *P. ostreatus* and *P. chrysosporium*, namely, the *Pleurotusostreatus* and *Phanerochaetechrysosporium*, for treating wastewater.

For the present invention, wastewater is understood to be those wastewaters contaminated with color, heavy metals, chemical oxygen demand (COD), and biological oxygen demand (BOD).

These strains were gradually adapted to tolerate high concentrations of heavy metals, such as Cr, Cd, Ni and Pb, for the treatment of wastewaters contaminated with color, heavy metals, chemical oxygen demand, and biological oxygen demand. This combination enables to fully cover the spectrum of degradation of azo, triphenylmethane, aniline or anthraquinone colorants, among others; having the advantage that it removes colorants alone or mixtures thereof from wastewaters, even in the presence of additives. This surprising effect is reflected in color units, settleable solids, $DBO_5$ and COD of industrial wastewaters treated with the consortium of fungi of the invention (Example 1).

In another aspect, the invention discloses a laminar biocarrier made by weaving or interlacing sisal yarns holding and immobilizing wood-decay fungi, namely, *Pleurotusostreatus* and *Phanerochaetechrysosporium* strains. The biocarrier is made by weaving or interlacing sisal yarns forming an elastic, flexible, resistant mesh that increases its porosity and malleability due to the treatment. These meshes are coated with a thin white-rot fungi paste biomass layer, namely, but not limited to, *P. ostreatus, P. chrysosporium, Trametesversicolor, Ganodermalucidum, Lentulaedodes, Phlebia radiata* and *Irpexlacteus*, which are hypertolerant to adaptive heavy metals (Cd, Ni, Pb, Cu and Cr), laccase producers, lignin peroxidase, and manganese peroxidase with bleaching and adsorption capacity.

Fungal growth extends over the entire surface of the mesh and through the pores through a penetration process, generating at the end of the production a sisal sheet coated on both sides with a white cottony, thin mycelium of the two fungal consortium. This laminar biocarrier made from sisal can be used as a filter in reactors with different configurations, such as cylindrical and square, for the treatment of industrial wastewater effluents.

Said filter for treating wastewaters contaminated with color, heavy metals and high values of chemical oxygen demand and biological oxygen demand comprises:

(a) a laminar biocarrier with an elastic, flexible and resistant mesh shape made by weaving or interlacing lignocellulosic yarns holding and immobilizing a biomass layer of the wood-decay fungi, namely, *Pleurotus ostreatus* and *Phanerochaete chrysosporium* strains.

(b) a support allowing the adjustment and assembly of the laminar biocarrier to reactors with different configurations such as cylindrical and square.

Laminar biocarriers are placed on a support inside the reactors, forming the filter, which can be used for up to three cycles of continuous operation.

Said biocarrier can be used to remove the color generated by azo, triphenylmethane, aniline or anthraquinone colorants, among others. With the advantage that it removes colorants alone or mixtures thereof from wastewater having additives.

Furthermore, the biocarrier of the invention has important adsorption properties by the joint action of the lignocellulosic material, the viable and hypertolerant biomass of both fungi, through which heavy metals such as Cd, Ni, Pb, Cu and Cr can be efficiently removed, keeping its efficiency by several cycles of operation.

In another aspect, the invention teaches a method for preparing the laminar biocarrier made from sisal yarns, comprising the steps of:

1. Preparing the support: previously washed and dried lignocellulosic yarns from 1 to 10 mm were chosen. Subsequently, a mesh with a pore size from about 0.1 mm to 10 mm and a thickness from about 1 and 15 mm according to specific requirements and processing conditions was made.
2. Sterilizing the support: meshes are sterilized by warm heat using two thermal cycles in autoclave (0.72 kPa) for about 15 minutes and 90 minutes (each cycle). The system is cooled and left closed until being inoculated with the fungal biomass.
3. Producing biomass: vials containing discs with biomass grown in *Pleurotusostreatus* and *Phanerochaetechrysosporium*, respectively, were taken from the primary strain bank, and planted under sterile conditions in wheat bran extract agar pH 6.5, and incubated for 8 days at 30° C. Growing and planting of each strain was performed separately. The spread of each strain is performed according to the conditions reported by Pedroza M et al in International Biotechnology Color Journal 1(1), 9-19, 2011 in the article entitled "Removal of reactive black 5 dye by *T. versicolor* immobilized on Luffacylindrica sponge and homogeneous photocatalysis with $TiO_2$." Agar discs with biomass obtained are subjected to spheronisation process (pelletization) and at the end thereof, the biomass is recovered by filtration under sterile conditions, and washed 3 times with sterile distilled water. In another container called homogenizer the *P. ostreatus* and *P. chrysosporium* biomass is mixed in the ratio 1:1, and mixed for 30 seconds until a uniform paste composed of consortium biomass is reached.
4. Colonizing the support: aluminum trays are uncovered and sisal meshes are carefully removed, all under sterile conditions.
    Then, a layer of a wheat bran extract agar from about 1 and 10 mm thick is added, and jellified for 10 minutes; subsequently, the sisal mesh is placed again on the agar surface and pressed until the polymer is attached. Once the support is arranged on the agar, a thin biomass layer is evenly distributed in areas equivalent to 0.01 to 0.5% (mass/volume) over all the mesh, and covered trays are incubated for about 5 to 15 days at a about 25 and 35° C. At the end of the process, there is provided a white and wet mesh that is ready to be placed inside the reactor.

The skilled person will understand that, in step 3, for producing the biomass one can star from the mixture of two or more wood-decay fungi from the group consisting of *P. ostreatus, P. chrysosporium, Trametesversicolor, Ganodermalucidum, Lentulaedodes, Phlebia radiata* and *Irpexlacteus*.

It is also considered within the scope of the invention the use of consortium of *Pleurotusostreatus* and *Phanerochaetechrysosporium* strains immobilized on a laminar biocarrier made from sisal yarns or in a filter comprising the laminar biocarrier for treating waste effluents.

The following are scientific facts illustratively supporting the present invention, which should not be construed as limiting the invention.

Example 1. Removal of Color, Chemical Oxygen Demand and Biological Oxygen Demand in Wastewater Using a Fungal Consortium Supported on a Sisal Laminar Biocarrier The production of the viable laminar biocarrier was performed by following the protocol described in the previous sections, and the sheet obtained was placed parallel to the walls of a 14 liters pneumatic reactor; then, 10 liters of a previously characterized textile wastewater (Table 1) obtained from a textile industry that processes cotton fibers were added. The airflow and temperature was adjusted, and the water treatment was performed. The water used in the experiments was not pre-treated or pH adjusted, it was used as it comes out from the dyeing process.

The process was evaluated for 8 days by performing daily sampling during the experiment, the process was not carried out under sterile conditions, so that the viable biocarrier could interact with the microbial flora present in the wastewater such as would occur in a scale field process. In each of the samples the pH, temperature, color units, suspended solids, settleable solids, $BOD_5$, COD, total Ni, fats and oils were determined, and removal values were compared against reference values of resolution 3957 SDA (Bogota, Colombia), which regulates the conditions of wastewater discharge.

The following results correspond to the days of maximum removal for the treatment and controls.

TABLE 1

Physical and chemical tests for wastewater according to resolution 3957 SDA (Bogota, Colombia)

| PARAMETER | RESULT OF THE WATER AS IT COMES OUT FROM THE DYEING PROCESS | LIMITS RESOLUTION 3957 SDA |
|---|---|---|
| pH (units) | 7.5 | 5.0-9.0 |
| Temperature (° C.) | 28 | 30° |
| Color units | 5000 | 50 UC dilution 1/20 |
| Suspended solids (mg/L) | 890 | 600 |
| Settleable solids (mg/L) | 4 | 2 |
| $BOD_5$ (mg/L) | 2876 | 800 |
| COD (mg/L) | 5900 | 1500 |
| Total Ni (mg/L) | 45 | N.E |
| Fats and oils (mg/L) | 15.7 | 100 |
| $CuSO_4$ (mg/L) | 0.456 | 0.25 |
| $CdSO_4$ (mg/L) | 0.06 | 0.02 |
| Lead acetate (mg/L) | 0.521 | 0.1 |

* Not established

The treatments that were individually tested were wood-decay fungi *Pleurotus ostreatusy Phanerochaete chrysosporium* strains, immobilized on the sisal laminar biocarrier by using two adsorption controls: the support without fungal biomass, and the biocarrier inactivated by heat treatment at 24 h. Table 2 shows the removal parameters for each treatment and control; it can be seen that the individual treatment with the strains does not remove the color, or decrease settleable solids, DB0$_5$ and COD levels established in environmental legislation.

In addition, an experiment at different times and with three replicates in order to verify the reproducibility of the process for treating industrial wastewater by using the immobilized fungal consortium in the laminar biocarrier of the invention was performed. Table 4 shows removal parameters for each treatment (immobilized fungal consortium in

TABLE 2

Removal of parameters in wastewater individually treated with *Pleurotus ostreatus* and *Phanerochaete chrysosporiumde* strains (repeat 1, about three replicates)

| PARAMETER | VIABLE BIOCARRIER OF *P. OSTREATUS* AT 24 HOURS | INACTIVATED BIOCARRIER OF *P. OSTREATUS* AT 24 HOURS | VIABLE BIOCARRIER OF *P. CHRYSOSPORIUM* AT 24 HOURS | INACTIVATED BIOCARRIER OF *P. CHRYSOSPORIUM* AT 24 HOURS | LIMITS RESOLUTION 3957 SDA |
|---|---|---|---|---|---|
| pH (unit) | 5.6 | 6.7 | 5.8 | 6.6 | 5.0-9.0 |
| Temperature (° C.) | 29 | 29 | 28 | 28 | 30° |
| Color units | 789 | 2100 | 923 | 2789 | 50 UC dilution 1/20 |
| Supended solids (mg/L) | 234 | 365 | 287 | 400 | 600 |
| Settleable solids (mg/L) | 2 | 6 | 3 | 9 | 2 |
| BOD$_5$ (mg/L) | 1025 | 2167 | 1458 | 2784 | 800 |
| COD (mg/L) | 2398 | 3678 | 1876 | 3987 | 1500 |
| Total Ni (mg/L) | 7 | 16 | 14 | 20 | N.E |
| Fats and oils (mg/L) | 2 | 7 | 4 | 8 | 100 |

Also, the immobilized fungal consortium in the sisal laminar biocarrier was assessed by using two adsorption controls: the support without fungal biomass and the biocarrier inactivated by heat treatment at 72 h. Table 3 shows removal parameters for each treatment and control. It can be seen that treatment with the consortium of the invention reduces color units to a 180UC value, settleable solids to 2 mg/ml, DB0$_5$ to 789 mg/l and CDO 1478 mg/l, which are within the levels established in environmental legislation, except for the color units, which significantly decrease from the staring value (180UC vs 5000UC), and compared with the removal of individual strains 789UC and 923UC for *P. ostreatus* and *P. chrysosporium*, respectively.

the sisal laminar biocarrier) and adsorption control (support without fungal biomass and inactivated biocarrier by heat treatment at 72 h).

As can be seen, the removal values in the color units, settleable solids, DBO$_5$ and COD are very close to the values initially established and given in Table 3. These parameters are within the limits established within the environmental legislation, except for the color units, which significantly decrease from the staring value (200UC vs 5000UC), and compared with the removal of individual strains 789UC and 923UC for *P. ostreatus* and *P. chrysosporium*, respectively.

TABLE 3

Removal of parameters in wastewater treated with the consortium *Pleurotus ostreatus* and *Phanerochaete chrysosporium* immobilized in a sisal laminar biocarrier (repeat 1, about three replicates)

| PARAMETER | VIABLE BIOCARRIER AT 24 HOURS | INACTIVATED BIOCARRIER AT 72 HOURS | SUPPORT WITHOUT BIOMASS AT 72 HOURS | LIMITS RESOLUTION 3957 SDA |
|---|---|---|---|---|
| pH (units) | 5.9 | 7.1 | 6.9 | 5.0-9.0 |
| Temperature (° C.) | 27 | 25 | 8 | 30° |
| Color units | 180 | 2387 | 4000 | 50 UC dilution 1/20 |
| Suspended solids (mg/L) | 367 | 467 | 478 | 600 |
| Settleable solids (mg/L) | 2 | 5 | 10 | 2 |
| BOD$_5$ (mg/L) | 789 | 1834 | 2981 | 800 |
| COD (mg/L) | 1478 | 4156 | 5023 | 1500 |
| Total Ni (mg/L) | 12 | 28 | 34 | N.E |
| Fats and oils (mg/L) | 3.6 | 10.4 | 13 | 100 |
| CuSO$_4$ (mg/L) | 0.1 | 0.211 | 0.312 | 0.25 |
| CdSO$_4$ (mg/L) | 0.005 | 0.04 | 0.05 | 0.02 |
| Lead acetate (mg/L) | 0.065 | 0.311 | 0.3 | 0.1 |

TABLE 4

Removal of treated wastewater parameters with the consortium
Pleurotus ostreatus and Phanerochaete chrysosporium immobilized
on a sisal laminar (repeat 2 average of three replicates)

| PARAMETER | VIABLE BIOCARRIER AT 24 HOURS | INACTIVATED BIOCARRIER AT 72 HOURS | SUPPORT WITHOUT BIOMASS AT 72 HOURS | LIMITS RESOLUTION 3957 SDA |
|---|---|---|---|---|
| pH (units) | 5.3 | 6.8 | 6.7 | 5.0-9.0 |
| Temperature (° C.) | 28 | 26 | 27 | 30° |
| Color units | 200 | 2400 | 3900 | 50 UC dilution 1/20 |
| Suspended solids (mg/L) | 345 | 500 | 400 | 600 |
| Settleable solids (mg/L) | 1 | 7 | 5 | 2 |
| $BOD_5$ (mg/L) | 924 | 1956 | 2100 | 800 |
| COD (mg/L) | 1657 | 4234 | 5123 | 1500 |
| Total Ni (mg/L) | 11 | 31 | 27 | N.E |
| Fats and oils (mg/L) | 4 | 9 | 11 | 100 |
| $CuSO_4$ (mg/L) | 0.129 | 0.234 | 0.390 | 0.25 |
| $CdSO_4$ (mg/L) | 0.009 | 0.02 | 0.03 | 0.02 |
| Lead acetate (mg/L) | 0.078 | 0.365 | 0.454 | 0.1 |

By comparing the results obtained with the biocarrier with viable biomass with other conventional treatment systems for wastewaters contaminated with textile dyes, it was observed that the biocarrier is more efficient because it leaves the effluents suitable for dumping in only 24 hours. While for obtaining similar or better removals, bacteria require 7 to 8 days (WijetungaSomasiri et al. "Evaluation of the efficacy of upflow anaerobic sludge blanket reactor in removal of colour and reduction of COD in real textile wastewater." Bioresource Technology 99 (2008), pp. 3692-3699.

Biocarrier with a comparison of a system using simultaneous wood degrading fungi and bacteria to treat wastewater textiles as described by CenekNovotny et al was also carried out: "Potential of fungal and bacterial combined treatment for removal Color in textile wastewater". Bioresource Technology 102 (2011) pp. 879-888 and shown to fungal bacterial system is efficient in removing color but with retention times between 5 and 7 days longer than those obtained with the consortium Phanerochaete chrysosporium and Pleurotus ostreatus according to the present invention.

A comparison of the biocarrier with a system simultaneously using wood degrading fungi and bacteria for the treatment of textile wastewaters as described by CenekNovotny et al: "Potential of combined fungal and bacterial treatment for color removal in textile wastewater." (Bioresource Technology 102 (2011) pp. 879-888) was also carried out, and it was found that the fungal bacterial system is efficient in removing color but with retention times between 5 and 7 days, which are longer than those obtained with the consortium Pleurotusostreatus and Phanerochaetechrysosporium according to the present invention.

The invention claimed is:

1. A laminar biocarrier for the treatment of wastewaters with an elastic, flexible and resistant mesh shape, wherein said laminar biocarrier is prepared by weaving or interlacing lignocellulosic yarns, and holds and immobilizes a wood-decay fungi biomass layer.

2. The laminar biocarrier of claim 1, wherein the immobilized wood-decay fungi fungal are selected from the group consisting of one or more of Pleurotus ostreatus, Phanerochaete chrysosporium, Trametes versicolor, Ganoderma lucidum, Lentula edodes, Phlebia radiata and Irpex lacteus.

3. The laminar biocarrier of claim 2, wherein the immobilized wood-decay fungi strains are Pleurotus ostreatu, and Phanerochaete chrysosporium.

4. The laminar biocarrier of claim 1, wherein the biomass layer in area is equivalent to a ratio of 0.01 to 0.5% (mass/volume) over the entire laminar biocarrier.

5. A filter for treating wastewaters comprising
(a) a laminar biocarrier according to claim 1; and
(b) a support allowing adjustment and assembly of the laminar biocarrier to a reactor for carrying out the treatment.

6. Method for preparing the laminar biocarrier of claim 1 which comprises:
1) preparing a support by taking previously washed and dried lignocellulosic material from about 1 to 10 mm to form a mesh of any shape with a pore size between 0.1 mm and 10 mm;
2) sterilizing the support with warm heat by applying two thermal cycles by autoclaving at 0.72 KPa for 15 minutes and 90 minutes each, and cooling a system by leaving the autoclave closed until the support is inoculated with the fungal biomass;
3) mixing biomass of two or more wood-decay fungi until a uniform paste of a consortium biomass is reached; and
4) colonizing the support under sterile conditions by adding a layer from about 1 and 10 mm thick of wheat bran extract agar, and jellifying for 10 minutes; placing another lignocellulosic mesh on the surface of the agar and uniformly inoculating sisal meshes with a biomass layer in areas equivalent to 0.01 to 0.5% (mass/volume), and incubating for 5 to 15 days at a temperature of about 25 and 35° C.

7. The method for preparing the laminar biocarrier of claim 5, wherein in step (1) final meshes may have different thickness dimensions from about 1 and 15 mm.

8. A method of treating wastewaters contaminated with color, heavy metals and high values of chemical oxygen demand and biological oxygen demand, which comprises contacting said wastewaters with combination of Pleurotus ostreatus and Phanerochaete chrysosporium in a laminar biocarrier of claim 1.

9. A method of treating wastewaters contaminated with color, heavy metals and high values of chemical oxygen demand and biological oxygen demand, which comprises contacting said wastewaters with a laminar biocarrier of claim 1 in reactors with different configurations.

10. A method of treating wastewaters contaminated with color, heavy metals and high values of chemical oxygen demand and biological oxygen demand, which comprises contacting said wastewaters with a filter of claim 5 in reactors with different configurations.

11. The laminar biocarrier of claim 2, wherein the biomass layer in areas are equivalent to a ratio of 0.01 to 0.5% (mass/volume) over the entire laminar biocarrier.

12. The laminar biocarrier of claim 3, characterized in that the biomass layer in areas are equivalent to a ratio of 0.01 to 0.5% (mass/volume) over the entire laminar biocarrier.

13. A filter for treating wastewaters comprising:
   (a) a laminar biocarrier according to claim 2; and
   (b) a support allowing adjustment and assembly of the laminar biocarrier to a reactor for carrying out the treatment.

14. A filter for treating wastewaters comprising:
   (a) a laminar biocarrier according to claim 3; and
   (b) a support allowing adjustment and assembly of the laminar biocarrier to a reactor for carrying out the treatment.

15. A filter for treating wastewaters comprising:
   (a) a laminar biocarrier according to claim 4; and
   (b) a support allowing adjustment and assembly of the laminar biocarrier to a reactor for carrying out the treatment.

16. Method for preparing the laminar biocarrier of claim 2 which comprises:
   1) preparing a support by taking previously washed and dried lignocellulosic material from about 1 to 10 mm to form a mesh of any shape with a pore size between 0.1 mm and 10 mm;
   2) sterilizing the support with warm heat by applying two thermal cycles by autoclaving at 0.72 KPa for 15 minutes and 90 minutes each, and cooling a system by leaving the autoclave closed until the support is inoculated with the fungal biomass;
   3) mixing biomass of two or more wood-decay fungi until a uniform paste of a consortium biomass is reached; and
   4) colonizing the support under sterile conditions by adding a layer from about 1 and 10 mm thick of wheat bran extract agar, and jellifying for 10 minutes; placing another lignocellulosic mesh on the surface of the agar and uniformly inoculating sisal meshes with a biomass layer in areas equivalent to 0.01 to 0.5% (mass/volume), and incubating for 5 to 15 days at a temperature of about 25 and 35° C.

17. Method for preparing the laminar biocarrier of claim 3 which comprises:
   1) preparing the support by taking previously washed and dried lignocellulosic material from about 1 to 10 mm to form a mesh of any shape with a pore size between 0.1 mm and 10 mm;
   2) sterilizing the support with warm heat by applying two thermal cycles by autoclaving at 0.72 KPa for 15 minutes and 90 minutes each, and cooling a system by leaving the autoclave closed until the support is inoculated with the fungal biomass;
   3) mixing biomass of two or more wood-decay fungi until a uniform paste of a consortium biomass is reached; and
   4) colonizing the support under sterile conditions by adding a layer from about 1 and 10 mm thick of wheat bran extract agar, and jellifying for 10 minutes; placing another lignocellulosic mesh on the surface of the agar and uniformly inoculating sisal meshes with a biomass layer in areas equivalent to 0.01 to 0.5% (mass/volume), and incubating for 5 to 15 days at a temperature of about 25 and 35° C.

18. A method of treating wastewaters contaminated with color, heavy metals and high values of chemical oxygen demand and biological oxygen demand, which comprises contacting said wastewaters with a laminar biocarrier of claim 2 in reactors with different configurations.

19. A method of treating wastewaters contaminated with color, heavy metals and high values of chemical oxygen demand and biological oxygen demand, which comprises contacting said wastewaters with a laminar biocarrier of claim 3 in reactors with different configurations.

* * * * *